US00PP10016P

United States Patent [19]

Brookfield et al.

[11] Patent Number: Plant 10,016

[45] Date of Patent: Sep. 2, 1997

[54] APPLE VARIETY BAIGENT

[75] Inventors: Barbara Christine Brookfield; Paul Leighton Purchas Brookfield, both of Havelock North, New Zealand

[73] Assignee: Brookfield New Zealand Limited, Hawkes Bay, New Zealand

[21] Appl. No.: 496,381

[22] Filed: Jun. 29, 1995

[51] Int. Cl.[6] ..... A01H 5/00

[52] U.S. Cl. ..... Plt./34.1

[58] Field of Search ..... Plt./34.1

[56] References Cited

U.S. PATENT DOCUMENTS

| | | | |
|---|---|---|---|
| P.P. 3,637 | 10/1974 | McKenzie | Plt./34.1 |
| P.P. 4,121 | 10/1977 | Ten Hove | Plt./34.1 |
| P.P. 6,172 | 5/1988 | Creech | Plt./34.1 |
| P.P. 7,396 | 12/1990 | Cooper | Plt./34.1 |
| P.P. 8,621 | 3/1994 | Olsen et al. | Plt./34.1 |
| P.P. 8,673 | 4/1994 | Waliser | Plt./34.1 |
| P.P. 8,720 | 5/1994 | Hill | Plt./34.1 |

*Primary Examiner*—James R. Feyrer
*Attorney, Agent, or Firm*—Quarles & Brady

[57] ABSTRACT

A new variety of apple originating as a limb mutation of Royal Gala (Tenroy cultivar, U.S. Pat. No. P.P. 4,121) is described. The variety was chosen for the unique combination of characteristic exhibited by the fruit. They are distinguished by particularly early red coloring throughout the tree, and have a distinctive appearance of predominantly bright red color and flecks of ground color overlain by a bold darker red stripe pattern that extends over the entire fruit.

8 Drawing Sheets

SUMMARY OF THE INVENTION

The present invention relates to a new and distinct apple variety. More particularly, the new cultivar is designated Baigent and is a limb mutuation of Royal Gala (Tenroy cultivar), U.S. Pat. No. P.P. 4,121. It was discovered in January 1985, on the owners' orchard in Hawkes Bay, New Zealand. The mutation was discovered in a block of trees planted in 1980 on MM106 rootstock, being part of the original release of FSV (free of specified virus) Royal Gala trees available in New Zealand. The mutation was originally noticed by the extremely early bright red color development of the fruit which made them stand out visually from the surrounding fruit. The fruit also had a different pattern of coloring comprised of bold darker red stripes with flecks of ground color showing through. The appearance was notable as the distinctive pattern extended over the entire surface of the apple. These attributes were recognized as being desirable traits for both the production and marketing of high quality apple fruit.

Budwood was taken from the limb at the time of discovery and 7 trees were propagated onto M793 rootstock. These trees were planted July 1986 on the owners' property and produced their first crop of apples in 1988. The fruit from these trees was true to type and consistent with the fruit found on the original mutation. In January 1989 budwood was taken and budded onto M793 rootstock to produce over 300 second generation trees. These trees were planted in 1990 in Hastings, Hawkes Bay, New Zealand. Fruit from these trees have exhibited the early fruit color development and distinctive appearance of the original mutation over successive seasons. Third generation trees have produced fruit demonstrating the same characteristics as those of the original mutuation, and of the first and second generation trees. These systematic observations of the fruiting characteristics over three asexually propagated generations spanning eleven years demonstrates that the unique combination of characteristics is established and transmitted through successive generations.

Comparative varietal evaluations have been conducted both by the inventors and the New Zealand Apple and Pear Marketing Board at Hastings in Hawkes Bay, the largest apple growing region in New Zealand and the major center for new apple cultivar evaluation in New Zealand. The climate at Hawkes Bay is relatively mild due to maritime influence, and very fertile soils contribute to vigorous growing conditions. Such conditions are suited to comparative studies of red color varieties as they are conductive to delayed and more variable red color development, compared to that achievable in most other countries and regions (such as the Pacific Northwest of the US) with their continental climate pattern.

The Baigent variety has been thoroughly compared to the parent Royal Gala (Tenroy cultivar, U.S. Pat. No. P.P. 4,121) and similarly derived varieties including the most closely related prior art apple Galaxy (U.S. Pat. No. P.P. 6,955) grown in New Zealand. These comparisons were made under identical conditions over several seasons. Comparisons were made with varieties Obrogala (U.S. Pat. No. P.P. 8,621), Treco Spur Red Gala No. 42 (U.S. Pat. No. P.P. 7,396) and Waliser Gala (U.S. Pat. No. P.P. 8,673) on the basis of the descriptions and recorded differences relative to Royal Gala and Galaxy as recited in the specification of the respective U.S. Plant Patents. The new variety has been named Baigent.

The invention may be more fully understood by having reference to the accompanying colour photographic representations, wherein.

DETAILED DESCRIPTION

The following is a detailed description of the new variety with colour terminology in accordance with Munsell Notation except where general terms of ordinary dictionary significance are used.

Figure 1:
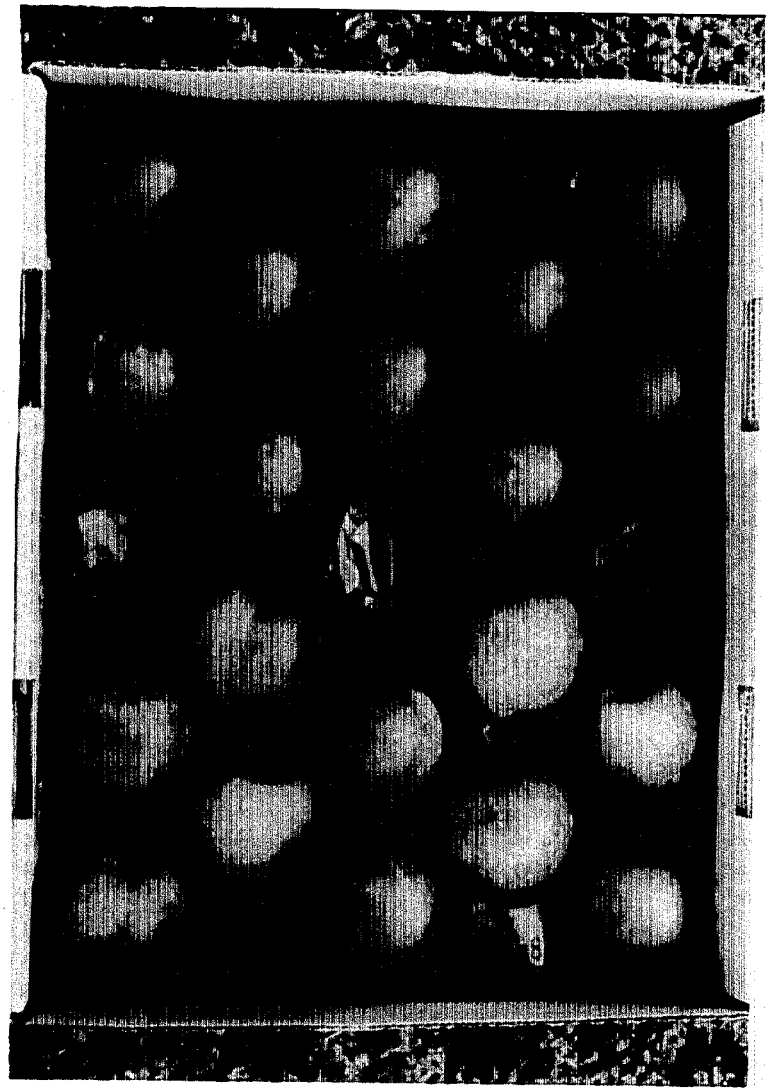
FIG. 1 is a photograph comparing the early color development of Baigent fruit (top) with comparable fruit from its parental variety Royal Gala (bottom), twenty days before harvest maturity.

The distinctive characeristics of the Baigent variety and the comparative differences with the prior varieties mentioned above are described as follows. Red color development of Baigent fruit occurs remarkably early. When compared at an immature stage of development Baigent fruit exhibit significantly earlier color development than Royal Gala fruit, 20 days ahead of the stage at which Royal Gala achieves mature coloration (FIG. 1). The fruit also have much higher red color coverage than those of Royal Gala when compared at similar maturity on successive dates leading up to harvest maturity (Table 1a). During maturation markedly more Baigent fruit achieve full coverage of the red coloring pattern by a given harvest date than either Royal Gala, which typically does not achieve full color coverage, or Galaxy (Table 1b). In comparision, Obrogala and Waliser Gala develop color 10 days earlier than Royal Gala, and Treco Spur Red Gala No. 42 (Treco Gala) claims higher percentage red color than Royal Gala, but relative earliness of coloring is not distinguished. These comparisons indicate that the higher red coloring characteristic develops earlier in the Baigent variety than either its parent Royal Gala or the prior art varieties.

TABLE 1

Red color comparison of cultivars[1].
(a) Red color development in relation to maturity.

| Harvest date | Variety | IEC (ul/l)[2] | Surface area covered by color pattern (%) |
|---|---|---|---|
| 2-13-92 | Baigent | 0.36 | 80 |
| | Royal Gala | 0.39 | 35 |
| 2-20-92 | Baigent | 0.91 | 95 |
| | Royal Gala | 0.80 | 60 |

(b) Proportion of fruit with full coverage of color pattern (%)

| Variety | Harvest date 2-13-96 | 2-20-96 | 2-27-96 | 3-5-96 |
|---|---|---|---|---|
| Baigent | 10 | 55 | 100 | 100 |
| Royal Gala | 0 | 0 | 0 | 0 |
| Galaxy | 10 | 15 | 20 | 65 |

[1]Average values of 20 fruit samples randomly selected from 10 representative trees.
[2]IEC: Internal ethylene concentration is a measure of physiological maturity.

Figure 2:
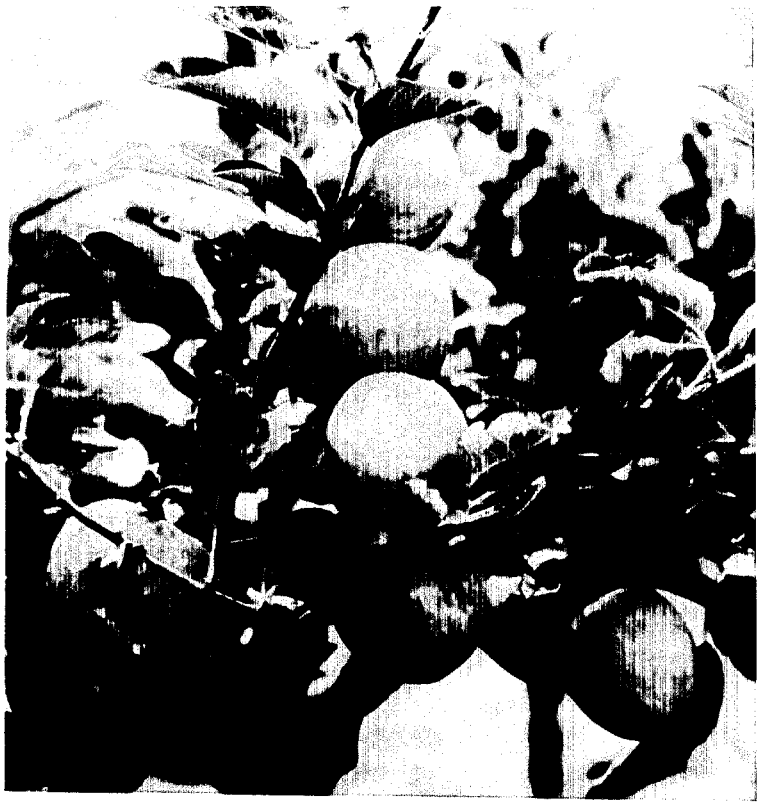
FIG. 2 is a photograph of a branch showing the uniform development of color pattern on Baigent fruit just prior to harvest.
Figure 3:
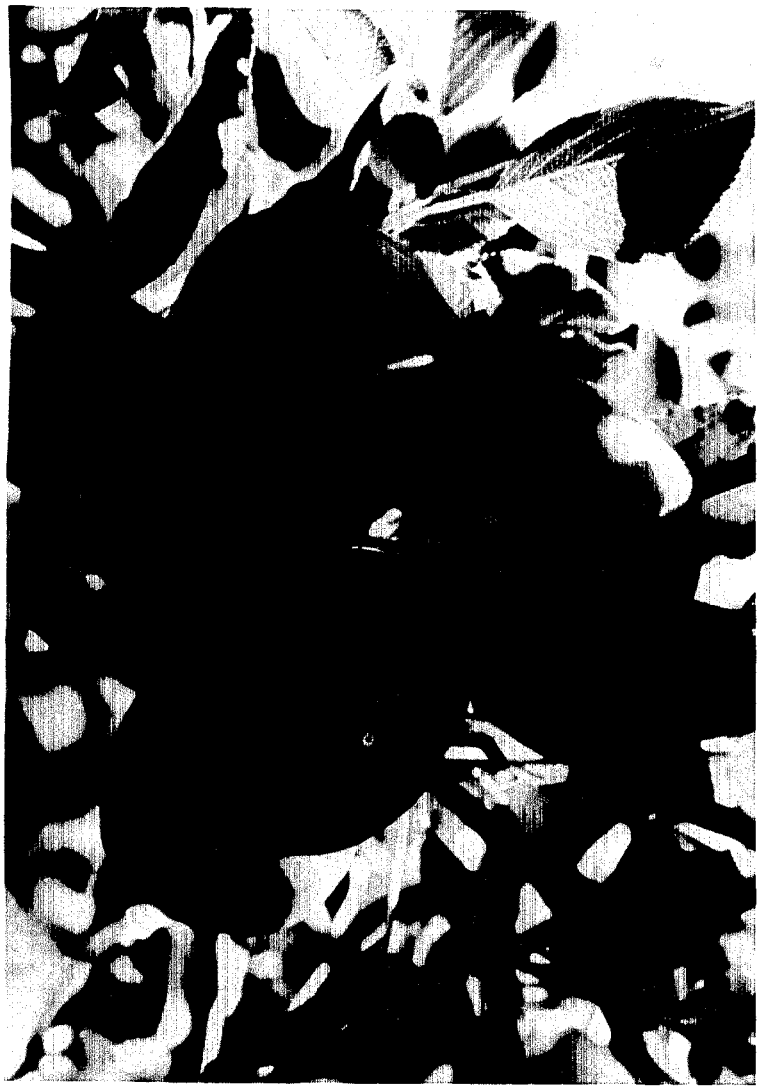
FIG. 3 is a photograph illustrating the superior ability of Baigent fruit to develop the characteristic color pattern even on the underside of fruit in shaded parts of the plant canopy.
Figure 7:
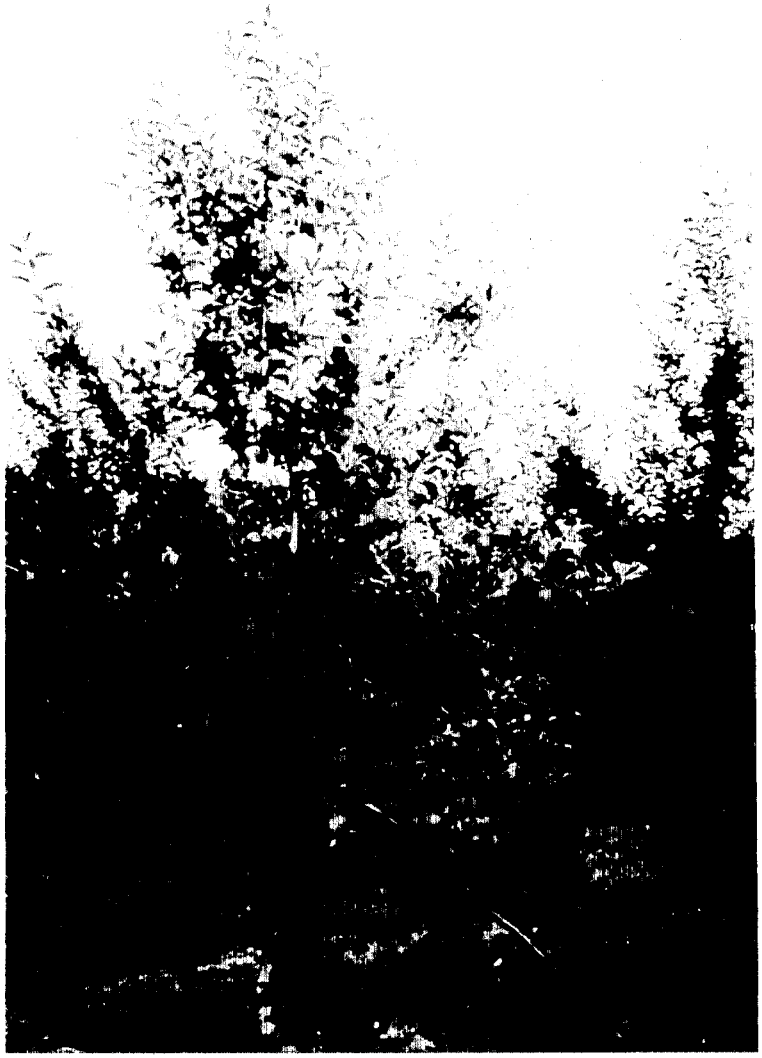
FIG. 7 is a photograph illustrating the Baigent tree form (foreground) and consistent coloration of the fruit at harvest as compared to Royal Gala fruit on the same age trees (background, left).

The early and high red coloring characteristic of the Baigent variety results in a particularly uniform appearance of fruits at maturity (FIG. 2). Baigent also shows superior ability to color both on the shaded side of individual fruits and in more shaded parts of the tree canopy (FIG. 3), leading to more consistent color throughout the tree canopy (FIG. 7). This differs from Royal Gala wich typically has fruit displaying a wider range of red color coverage at harvest leading to the need for more multiple picks to obtain consistent color. In comparison, Baigent can be harvested on fewer occasions, to a higher standard of color coverage, and within a shorter prior of time.

Figure 4:
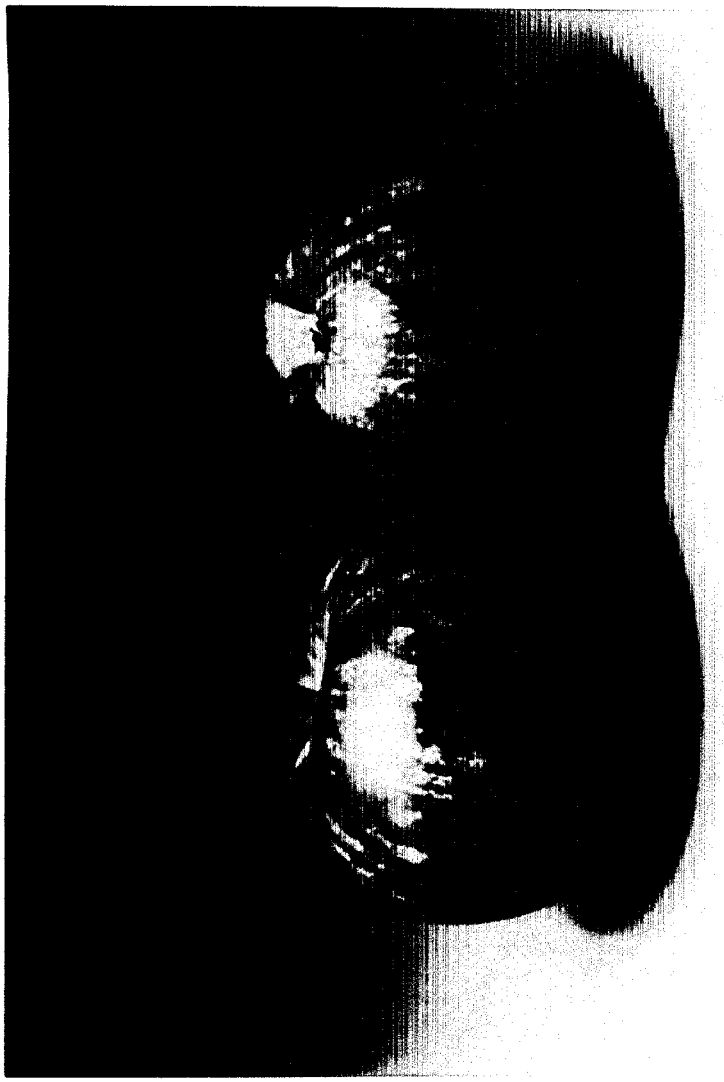
FIG. 4 illustrates the distinctive color pattern of Baigent fruit at harvest maturity with predominantly bright red color and patches of ground overlain by bold darker red striping.
Figure 5:
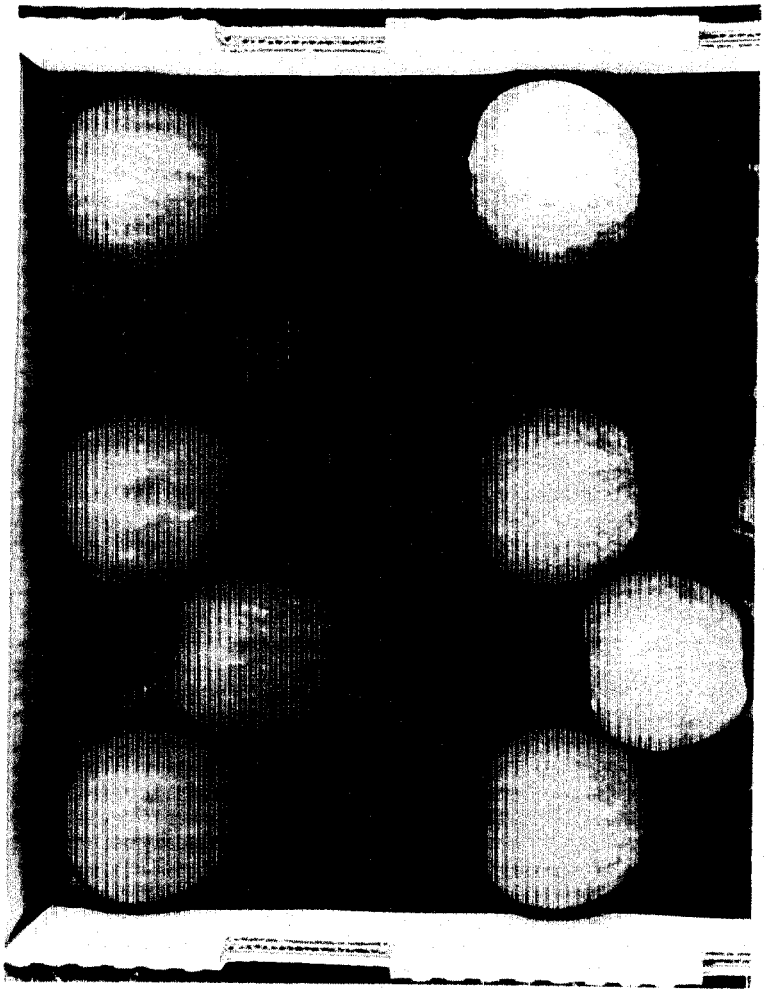
FIG. 5 is a photograph comparing fruit of Baigent (top) with fruit from Royal Gala (bottom) after storage, illustrating the most colored side (three fruit on the left) and least colored side (single fruit on the right) of the fruit.

Baigent fruit have a distinctive appearance. The color pattern extends more or less over the entire surface of the fruit and is of predominantly bright red color with flecks of ground color overlain by bold darker red striping (FIG. 4). Grown and compared under the same conditions, fruit of the parent Royal Gala do not develop color as comprehensively or evenly over the skin surface, and red coloration is generally less intense. Even when the most highly colored fruit samples are compared after storage, thus subject to factors that tend to minimize color differences, Baigent fruit still exhibit fuller red coloration while maintaining a striped effect (FIG. 5). Furthermore, Baigent fruit develop a redder hue (5 R 4.4/7, Munsell Color Notation System) than the more orange red color (7.5 R 4/8) of Royal Gala. Compared with Baigent, Galaxy fruit show a more solid cherry red coloration with indistinct dark red over-striping. Obrogala fruit exhibit a solid dark nopal red blush over 90–100% of the skin with a blushed undercolor and indeterminate striping considerably less distinct than that of the Tenroy cultivar. Most fruit show no striping when mature. In comparision, Baigent fruit have a bright red appearance and retain distinct striping when mature (FIG. 4), while the ground color is discrete rather than blushed as in Obrogala. Treco Gala have brilliant bright red color over 90% of the fruit with a red on red pattern and the appearance is of a soft muted stripe blending beneath the have a bright red color, whereas Baigent fruit retain a more separate pattern of red and darker red striping and background color that is more prominent than the muted red on red appearance of Treco Gala fruit. Waliser Gala fruit have a bright red finish with a faint, narrow, light red pinstripe pattern as described in the patent. In comparison, Baigent fruit have a prominent darker red stripe pattern, the stripes discontinuous and of variable width with more distinct edges rather than the narrow, more or less continuous and less distinct pinstripe pattern of Waliser Gala. In addition, Baigent fruit retain patches of background color characterized by small flecks of red giving these areas a speckled appearance (FIG. 4) quite unlike the blushed red on red pinstripe pattern of Waliser Gala.

The unique combination of early, high and more consisent coloring, and a color pattern comprising bold red striping with flecks of ground color, distinguish Baigent fruit from those of its less colored parent Royal Gala and the more blushed, subdued striping characteristics of the prior art varieties. These distinguishing attributes are of particular value as they offer a significant commercial advantage. Wastage and loss of quality from under colored and/or overmature fruit that occurs in the parent cultivar is minimized in Baigent. In particular, the distinctive color pattern is of a type highly desired in the market place compared to more blushed, less distinctively striped pattern of similarly derived varieties.

The Baigent variety matures at a similar time to the parent Royal Gala and Galaxy (Table 2). In contrast, Obrogala and Waliser Gala both mature 4 days ahead of Royal Gala. When compared on the same harvest dates with Royal Gala, their starch pattern indices are higher, whereas starch pattern indices for Baigent are similar or lower, emphasizing the difference in maturity. Under similar conditions, Gala matures slightly earlier than Royal Gala. As Treco Gala is derived from Gala and is of spur type growth habit — both factors that lead to earlier maturity than standard Royal Gala — it would be expected to have earlier maturity than Baigent. The Baigent cultivar is distinctive in that these prior art cultivars mature earlier than Royal Gala wheereas Baigent does not, again emphasizing the early coloring characteristic of Baigent in relation to maturity.

TABLE 2

Maturity comparison of cultivars[1].

| Variety | Flesh firmness (lbs) | Soluble solids (%) | Starch pattern index (0–6) | Tritratable acidity (meg/100 ml) |
|---|---|---|---|---|
| (a) 1994[2] | | | | |
| Baigent | 20.0 | 9.8 | 1.0 | 6.0 |
| Royal Gala | 19.0 | 9.8 | 1.8 | 5.1 |
| Galaxy | 20.0 | 10.6 | 1.0 | 5.2 |
| (b) 1996[3] | | | | |
| Baigent | 16.5 | 10.4 | 2.3 | 6.0 |
| Royal Gala | 16.1 | 10.3 | 2.9 | 5.3 |
| Galaxy | 16.2 | 10.5 | 3.0 | 4.9 |

[1]Average values for harvests in each year; 20 fruit samples evaluated per cultivar per harvest.
[2]Represents 3 harvest dates; 2–17, 2–24, 3–3.
[3]Represents 5 harvest dates; 2–13, 2–20, 2–27, 3–5, 3–12.

Figure 6:
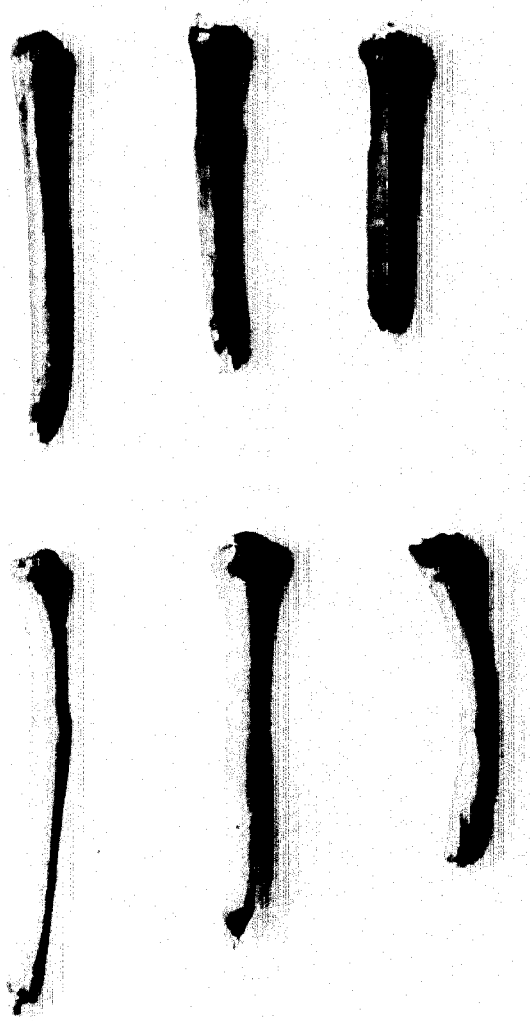
FIG. 6 is a photograph comparing the fruit stem color of Baigent (top) with Royal Gala (bottom) after storage.

At anthesis the stem and sepals of the Baigent flower are deep red in color whereas those of Royal Gala are green. This difference in stem color is apparent throughout fruit development (FIG. 1). The stems of Baigent fruit remain red (10 R 4.3/3) compared with the more yellow stems of Royal Gala (5 Y 5.6/4) after storage (FIG. 6). In comparison, the stems of Galaxy are slightly yellow-red in color (2.5 YR 4.2/3). Baigent fruit shape is similar to that of Royal Gala, but differs from Galaxy, which is slightly more round (Table 3), Obrogala which is more conical than Royal Gala, and Treco Gala which is substantially more round than Royal Gala. Treco Gala fruit are also recorded as larger in size than Royal Gala fruit, whereas Baigent has similar size fruit to Royal Gala.

Baigent fruit have excellent storage quality. At maturity, this is indicated by assessments that show tritratable acidity, which may fall rapidly during storage, is higher in Baigent than Royal Gala or Galaxy (Table 2). Comparative sensory assessment after storage (Massey University Food Technology Research Centre) found Baigent fruit to be significantly different compared to those of Royal Gala, having more acid balanced flavor and more crunchy texture, whereas Royal Gala and Galaxy were considered to have similar sensory characteristics. Baigent fruit have a bright white flesh color compared with that of Obrogala and Royal Gala (creamy white), Treco Gala (yellowish tint) and Waliser Gala (satiny white).

Figure 8:
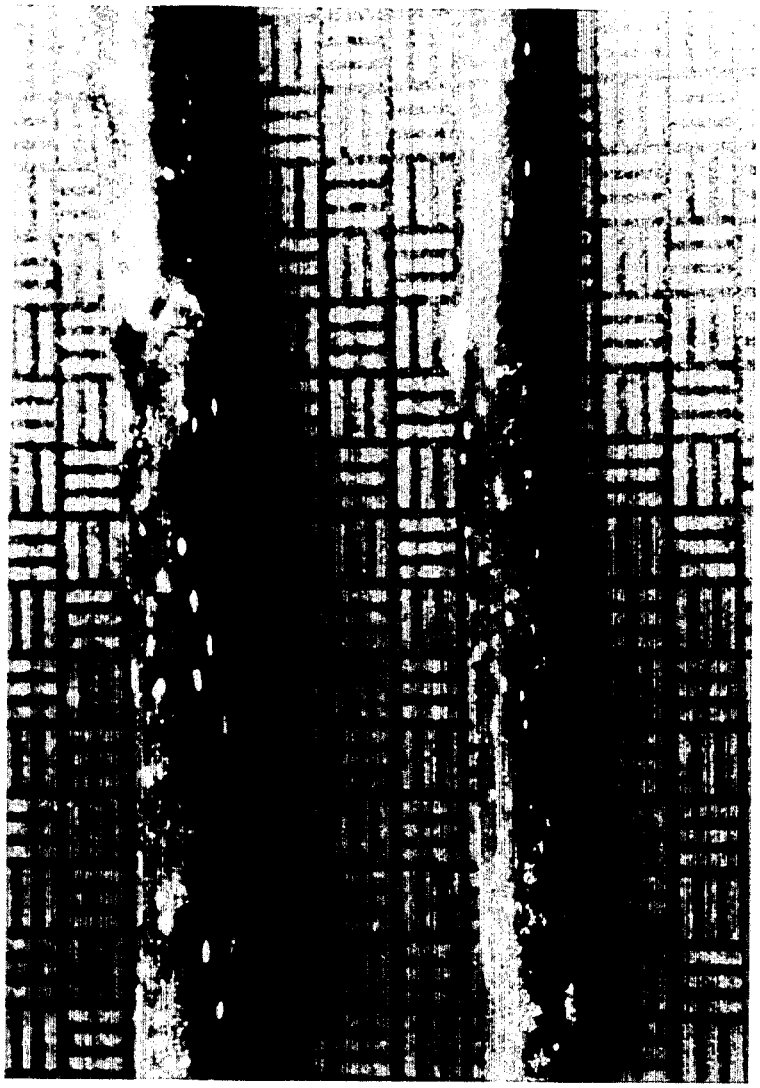
FIG. 8 is a photograph comparing the bark color and lenticels on one year old wood of Baigent (left) and Royal Gala (right).

The Baigent variety has a standard spreading growth habit like that of the parent Royal Gala (FIG. 7) and under the same growing conditions spur density is similar amongst Baigent, Galaxy and Royal Gala (Table 3). Treco Gala differs in growth habit by exhibiting pronounced spur type compact growth characteristics with higher spur densities than Royal Gala. The leaves and bark of the Baigent variety are distinguishable as being darker in color than those of Royal Gala or Galaxy when grown under the same conditions (Table 3, FIG. 8). In comparison, differences in leaf color between Waliser Gala and Royal Gala were not measurable, and no differences in bark color were noted. The bark lenticels of Baigent are of similar appearance to those of Royal Gala (FIG. 8), unlike the perpendicularly aligned and more rounded lenticels described and shown in the patent for Obrogala.

TABLE 3

Comparison of growth characteristics of cultivars (1996).

| Variety | Fruit shape (L:D)[1] | Spur density[2] | Leaf color[3] | Bark color[4] |
|---|---|---|---|---|
| Baigent | 0.91 | 14.5 | 7.5 GY 3.4/1 | 2.5 YR 5/1 |
| Royal Gala | 0.91 | 14.7 | 7.5 GY 3.6/2 | 2.5 YR 4/1 |
| Galaxy | 0.89 | 14.6 | 7.5 GY 3.6/2 | 2.5 YR 4/1 |

[1]Average value of length:diameter ratios in 60 fruit samples per cultivar at maturity. Galaxy significantly different ($p = 0.05$).
[2]Average number of spurs per square cm of branch cross-sectional area in 10 two year old lateral branches per cultivar (no significant difference).
[3]Average values of 10 leaves per variety at fruit maturity measured with a colorimeter. Presented in the Munsell Color Notation System.
[4]Average values of 10 samples per cultivar measured on 2 year old wood with a colorimeter. Presented in the Munsell Color Notation System.

Parentage: A natural limb mutation of apple variety Royl Gala (Tenroy U.S. Pat. No. P.P. 4,121).

Locality where grown and observed: Hawkes Bay, New Zealand.

Dates of first and last pickings: Normally between February 22 and March 3.

Tree: Medium small, spreading non-spur type growth, moderate vigor, hardy, productive, regular bearing on spurs and laterals.

Trunk: Medium stockiness, smooth.

Branches: Medium thickness, smooth, moderately branched.

*Lateral color (2 year old wood).*—Dark Brown, 2.5 Y 5/1.

Lenticels: Numerous, medium large, elongated, aligned parallel to the branch.

Leaves: Medium large, medium wide, medium length to width ratio, abruptly pointed. Length 12 cm, width 7 cm. Outward pose, medium glossiness of upper side, medium pubescence on lower side.

*Margin.*—Crenate, finely serrate.

*Petiole length.*—About 4 cm.

*Upper surface color.*—Dark Green 7.5 GY 3.4/1.

Flowers: Medium early. Dates of first and full bloom (southern hemisphere) October 5 and October 20 respectively.

*Size.*—Medium small. Flat shape when open, margins of petals touching.

*Color.*—Petals at tulip stage of opening 10 RP 9/2 (upper surface). Pink fading to white on reverse side. Single row, margins smooth.

*Stamens.*—Single row, filaments white, anthers yellow.

*Pistils.*—Stigma prominent, styles fused toward the base, pubescent.

*Sepals.*—Large, pointed, thick. Color: Red.

Fruit:

*Ripening.*—Early season. Over the period late-February to early-March in Hastings, Hawkes Bay.

*Size.*—Medium uniform. Axial diameter 6.9 cm. Transverse diameter 7.6 cm.

*Form.*—Globose, ribbing absent, weak-medium crowning at distal end.

*Cavity.*—Symmetrical, abrupt at base, apex acuminate. Depth 1.8 cm. Breadth 2.5 cm. Markings: none.

*Basin.*—Symmetrical, rounded, wide, undulate. Depth 0.6 cm. Markings: none.

*Stem.*—Medium stout, Length 2.5 cm. Breadth 0.3 cm. Color: Red, 10 R 4.3/3.

*Calyx.*—Closed. Segments: broadly lanceolate, reflexed from the base at apex. Outer surface: Pubescent. Inner surface: Pubescent.

*Skin.*—Medium thickness; smooth, glossy, waxed, greasiness absent.

*Lenticles.*—Inconspicuous, small, even, more numerous toward calyx, circular, pale yellow.

*Red color markings.*—Red (5 R 4.4/7) with darker red stripes (5 R 4/6).

*Bloom.*—Wanting.

*Scar-skin.*—Very light, white.

*General effect of color.*—Distinctive pattern of predominantly bright red color and flecks of ground color overlain with bold, discontinuous darker red striping.

*Flesh.*—Juicy, bright white, 10Y8/1. Texture: Firm, tender, fine and crisp.

*Flavor.*—Delicate, sweet, slight acidity.

*Aroma.*—Subtly aromatic.

*Quality.*—Best.

*Core.*—Sessile, medium. Bundle area (longitudinal section): Small, oblate. Bundles: Inconsicuous, in one whorl. Core lines: Clasping, cross section, moderately distinct. Calyx tube: Glabrous toward base, funnel form. Stem of funnel: Long. Depth of tube to shoulder: 0.5 cm. Entire depth: 1.3 cm. Styles: Present. Stamens: In one distinct whorl, median. Auxiliary cavity: Present. Seed cells: Axile, open. Cell Walls: Thin. Length 1.5 cm, breadth 0.5 cm.

*Seeds.*—Medium sized, light brown (5 YR 4/4 Munsell Notation). Number perfect: Number in one cell: 2. Length 0.9 cm. Breadth 0.5 cm.

Use: Dessert apple.

Keeping quality: Good.

Resistance to insects: Good.

Resistance to diseases: Good.

We claim:

1. A new and distinct variety of apple tree which is a mutation of the Royal Gala variety (Tenroy cultivar, U.S. Pat. No. P.P. 4,121) substantially as herein shown and described, characterized by:

(a) a distinctive color patern covering the fruit of predominantly bright red color and flecks of ground color overlain with bold, discontinuous darker red striping, (b) particularly early development of fruit red color extending throughout the tree at maturity; and (c) dark coloring of fruit stems, bark and leaves.

* * * * *

UNITED STATES PATENT AND TRADEMARK OFFICE

CERTIFICATE OF CORRECTION

PATENT NO. : PP 10,016

DATED : September 2, 1997

INVENTOR(S) : Brookfield New Zealand Limited.

It is certified that error appears in the above-identified patent and that said Letters Patent is hereby corrected as shown below:

Abstract Line 4: 'characteristic' should read 'characteristics'
Column 2 Line 6: 'conductive' should read 'conducive'
Column 3 Line 20: 'characeristics' should read 'characteristics'

Column 4 Line 7: 'wich' should read 'which'
Column 4 Line 39: should read 'blending beneath the red colour' - ie have a bright should be deleted from this line.
Column 5 Line 11: ' wheereas' should read 'whereas'
Column 6 Line 25: should read 'no significant differences'
Column 6 Line 30: 'Royl' should read 'Royal'
Column 8 Line 2: 'Inconsicuous' should read 'Inconspicuous'

Signed and Sealed this

Twenty-sixth Day of January, 1999

*Attest:*

*Attesting Officer*

*Acting Commissioner of Patents and Trademarks*